(12) United States Patent
Parker et al.

(10) Patent No.: US 7,566,342 B2
(45) Date of Patent: Jul. 28, 2009

(54) DELIVERY SYSTEM FOR MEDICAL DEVICE

(75) Inventors: Fred T. Parker, Unionville, IN (US); Palle Hansen, Bjaeverskov (DK); Nathaniel A. Irwin, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/965,210

(22) Filed: Dec. 27, 2007

(65) Prior Publication Data
US 2009/0171300 A1     Jul. 2, 2009

(51) Int. Cl.
*A61F 2/06* (2006.01)

(52) U.S. Cl. ..................................... 623/1.11

(58) Field of Classification Search ........ 623/1.11–1.23; 606/191–198; 600/433–435, 585
See application file for complete search history.

(56) References Cited

U.S. PATENT DOCUMENTS

| | | | | |
|---|---|---|---|---|
| 4,961,731 A | 10/1990 | Bodicky et al. | | 604/264 |
| 5,836,926 A | 11/1998 | Peterson et al. | | 604/282 |
| 5,931,811 A | 8/1999 | Haissaguerre et al. | | 604/95 |
| 5,957,865 A * | 9/1999 | Backman et al. | | 600/585 |
| 6,106,510 A | 8/2000 | Lunn et al. | | 604/525 |
| 6,146,415 A | 11/2000 | Fitz | | 623/1.11 |
| 6,240,231 B1 | 5/2001 | Ferrera et al. | | 385/115 |
| 6,325,790 B1 | 12/2001 | Trotta | | 604/523 |
| 6,663,614 B1 | 12/2003 | Carter | | 604/525 |
| 6,709,454 B1 | 3/2004 | Cox et al. | | 623/1.16 |
| 2004/0064130 A1 | 4/2004 | Carter | | 604/523 |
| 2005/0043712 A1 | 2/2005 | Devens, Jr. | | 604/525 |
| 2005/0115624 A1 | 6/2005 | Walak | | 138/139 |
| 2008/0045928 A1 * | 2/2008 | Simpson et al. | | 604/525 |

* cited by examiner

*Primary Examiner*—Kevin T Truong
(74) *Attorney, Agent, or Firm*—Brinks Hofer Gilson & Lione

(57) ABSTRACT

A system for delivery of a medical device to a target site within the body of a patient includes an introducer sheath, and a delivery assembly receivable within a passageway of the sheath. The delivery assembly comprises an inner tubular and an outer tubular member. At least a distal portion of the inner tubular member has a diameter such that the medical device is receivable thereover. The outer tubular member is generally coaxial with the inner tubular member, and has a length such that the outer tubular member distal end terminates proximal to the inner tubular member distal portion. The outer tubular member has a first outer diameter at the proximal end and extends for a length of the outer tubular member to a first diameter boundary point. The outer tubular member has a gradual inward taper in the distal direction from the boundary point to a second outer diameter, and has an abrupt outward taper in the distal direction from the second diameter to the first diameter.

15 Claims, 3 Drawing Sheets

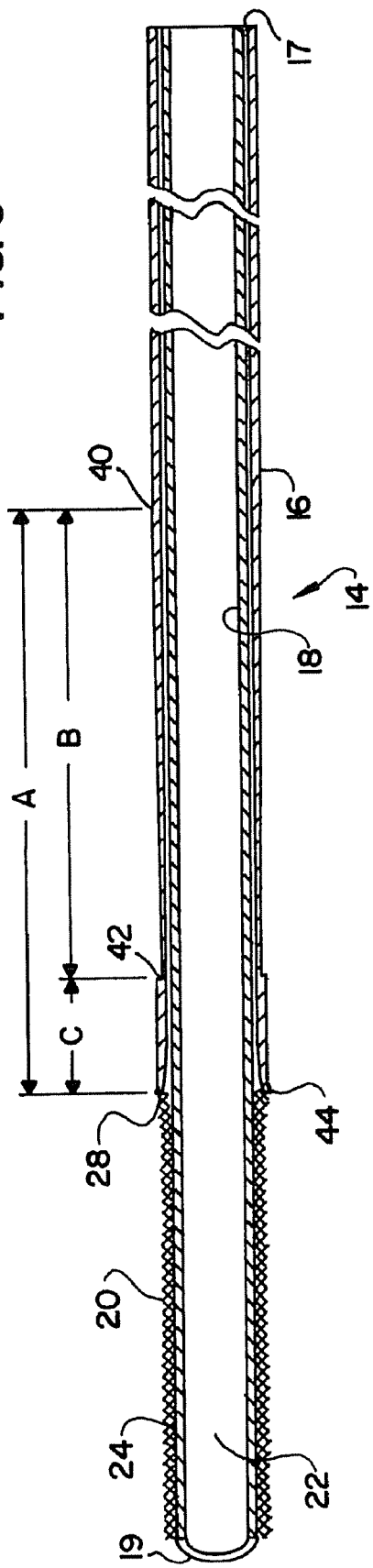

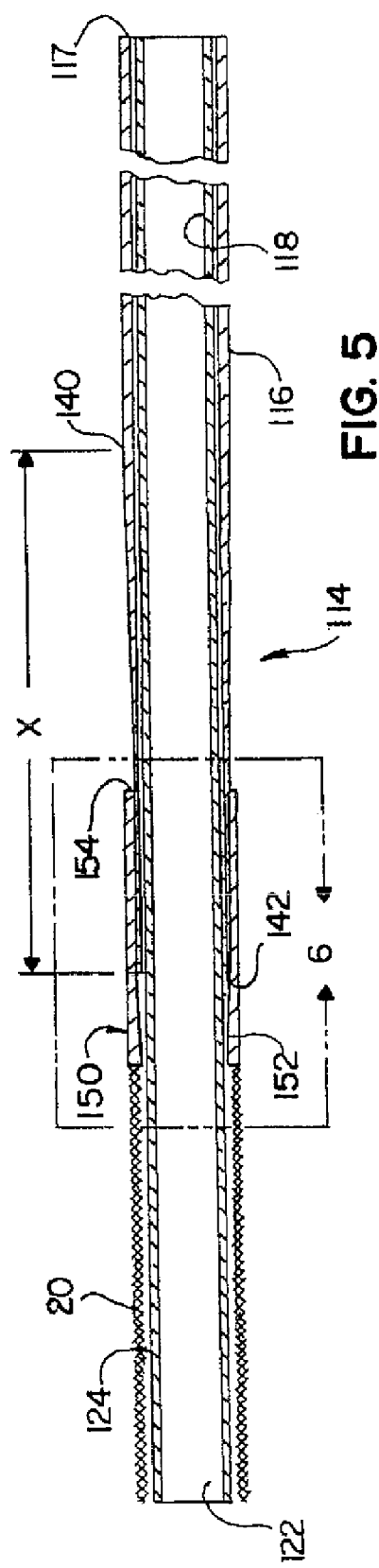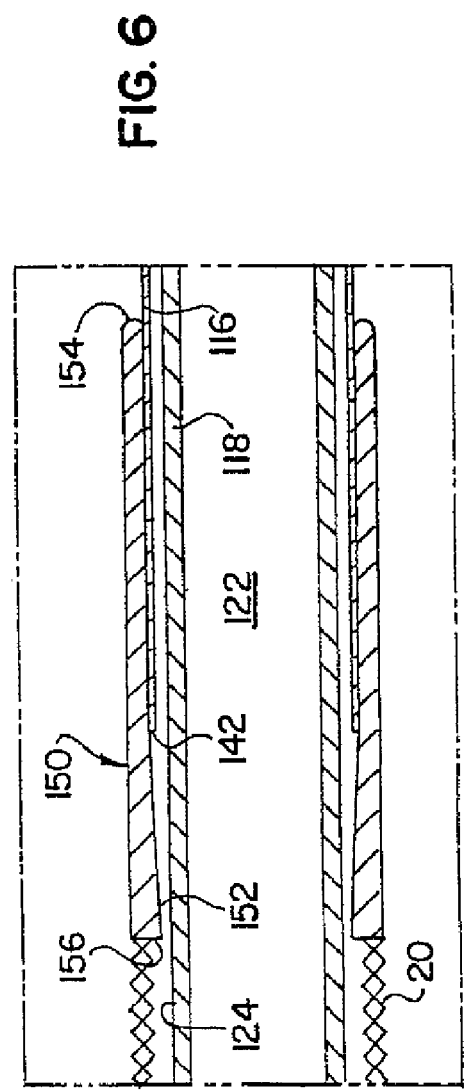

DELIVERY SYSTEM FOR MEDICAL DEVICE

BACKGROUND

1. Technical Field

The present invention relates to a delivery system for transporting a medical interventional device to a target site within the body of a patient. More particularly, the invention relates to a system of coaxial tubular members for delivering a medical device, such as a stent, into a designated lumen in the body of a patient to establish, or maintain, patency of the lumen.

2. Background Information

In modern medicine, interventional devices are often percutaneously introduced into the body of a patient via a suitable delivery apparatus, and delivered to a target site within the body for a medical purpose. One common example of a medical interventional device introduced in this manner is a stent. A stent is typically inserted into the lumen of a vessel or other bodily passageway to reinforce, repair, or otherwise provide support to establish or maintain the patency of the lumen. For example, when a patient suffers from atherosclerosis (hardening of the arteries), a stent may be placed in a coronary or a peripheral artery at a location where the artery is weakened, damaged or otherwise susceptible to collapse. The stent, once in place, reinforces that portion of the artery, thereby restoring normal blood flow through the vessel.

One form of stent which is particularly desirable for implantation in arteries and other body lumens is a cylindrical stent which is radially expandable upon implantation from a smaller first diameter to a larger second diameter. Radially expandable stents are typically loaded onto, or into, a delivery catheter, and fed internally through the arterial pathways of the patient until the unexpanded stent reaches the target site. Radially expandable stents are normally of two general types. One type, generally referred to as a "balloon-expandable" stent, is fitted in a compressed state over an uninflated balloon at the distal end portion of the delivery catheter. Once the catheter reaches the target site, the balloon is inflated by transmitting an inflation fluid through a lumen in the delivery catheter to the interior of the balloon. Upon inflation, the balloon exerts a radial pressure on the stent, thereby causing the compressed stent to radially expand to a larger diameter. Following expansion, the stent exhibits sufficient radial rigidity to remain in the expanded condition after the balloon has been deflated and the catheter has been removed.

The other type of radially expandable stent, generally referred to as a "self-expanding" stent, is formed from a resilient or shape memory material which is capable of self-expanding from a compressed state to an expanded state without the application of a radial outwardly-exerted force on the stent. Typically, a self-expanding stent is loaded into a delivery device that restrains the stent in the compressed state. Once the delivery device is directed to the target site, an ejection mechanism, such as a pusher, is employed to eject the stent from the distal end of the delivery device. Alternatively, an outer sheath of the delivery device is withdrawn such that it no longer covers the stent. In either event, once the stent is freed from the restraints of the device, it self-expands to the desired diameter.

The use of radially expandable stents advantageously allows the physician to insert relatively smaller diameter medical devices to prop up, reinforce or otherwise support relatively larger diameter vessels. However, the delivery of such stents to the target site has at times proven to be problematic. For example, the structure of a conventional delivery catheter may cause the catheter shaft to be subject to stress risers as it traverses the vessel. Stress risers comprise weakened or high stress segments of the catheter which may cause the catheter shaft to undesirably bend or otherwise fail during passage through the vessel. In a delivery system for a self-expanding stent that includes coaxial catheters, such high stress segments may occur, for example, at the point where the inner catheter meets the outer catheter. This typically occurs when the delivery system traverses a tortuous pathway in the body of the patient. In some cases, such as the bifurcation into the iliacs, the catheter is required to go around a high angle bend. In these instances, kinking and decreased trackability are prone to occur due to the high stress in the system as it attempts to traverse the high angle bend.

It is desired to provide a delivery system for a stent or other interventional medical device that avoids the problems of prior art devices.

SUMMARY

The problems of the prior art are addressed by the inventive delivery system. In one form thereof, the invention comprises an assembly for use in the delivery of a medical device to a target site within the body of a patient. The assembly comprises an inner tubular member having a distal portion sized to receive the medical device thereover. An outer tubular member is coaxial with the inner tubular member, and has a length such that the distal end of the outer tubular member distal end terminates proximal to the inner tubular member distal portion. The outer tubular member has a first outer diameter at its proximal end, and a gradual inwardly tapered portion in a distal direction to a second outer diameter. The outer tubular member then has an abrupt outward taper in the distal direction from the second diameter.

In another form thereof, the invention comprises a system for delivery of a medical device to a target site within the body of a patient. The delivery system includes an introducer sheath having a proximal end, a distal end, and a passageway extending therebetween. The introducer sheath has a length sufficient for insertion through a pathway in the body of the patient from an entry site to the target site. A delivery assembly is receivable within the sheath passageway for carrying the medical device. The delivery assembly comprises an inner tubular member having a proximal end and a distal end, at least a distal portion of the inner tubular member having a diameter such that the medical device is receivable thereover, and an outer tubular member having a proximal end and a distal end. The outer tubular member is generally coaxial with the inner tubular member and has a length such that the outer tubular member distal end terminates proximal to the inner tubular member distal portion. The outer tubular member has a first outer diameter at the proximal end and extends for a length of the outer tubular member to a first diameter boundary point. The outer tubular member has a gradual inward taper in the distal direction from the boundary point to a second outer diameter, and has an abrupt outward taper in the distal direction from the second diameter.

In still another form thereof, the invention comprises a delivery assembly for use in delivering a medical device to a target site within the body of a patient. The delivery assembly comprises an inner tubular member and an outer tubular member. At least a distal portion of the inner tubular member has a diameter such that the medical device is receivable thereover in a compressed condition. The outer tubular member is generally coaxial with the inner tubular member, and has a length such that the distal end of the outer tubular member terminates proximal to the inner tubular member distal portion. The outer tubular member has a first outer diameter at its proximal end, and has a gradual inwardly tapered portion in a distal direction to a second outer diameter. A holder band is disposed over the outer tubular member second diameter. The holder band is sized and arranged to maintain a position of the medical device on the inner tubular member.

BRIEF DESCRIPTION OF THE DRAWINGS

FIG. 3 is a longitudinal sectional view of the inner delivery assembly of the delivery system of FIG. 1;

FIG. 4 is an enlarged view of the distal end portion of the outer tube of the inner delivery assembly;

FIG. 5 is a longitudinal sectional view of an alternative embodiment of an inner delivery assembly for use in a delivery system; and FIG. 6 is an enlarged view of a portion of the inner delivery assembly of FIG. 5.

DETAILED DESCRIPTION OF THE DRAWINGS AND THE PRESENTLY PREFERRED EMBODIMENTS

Figure 1:
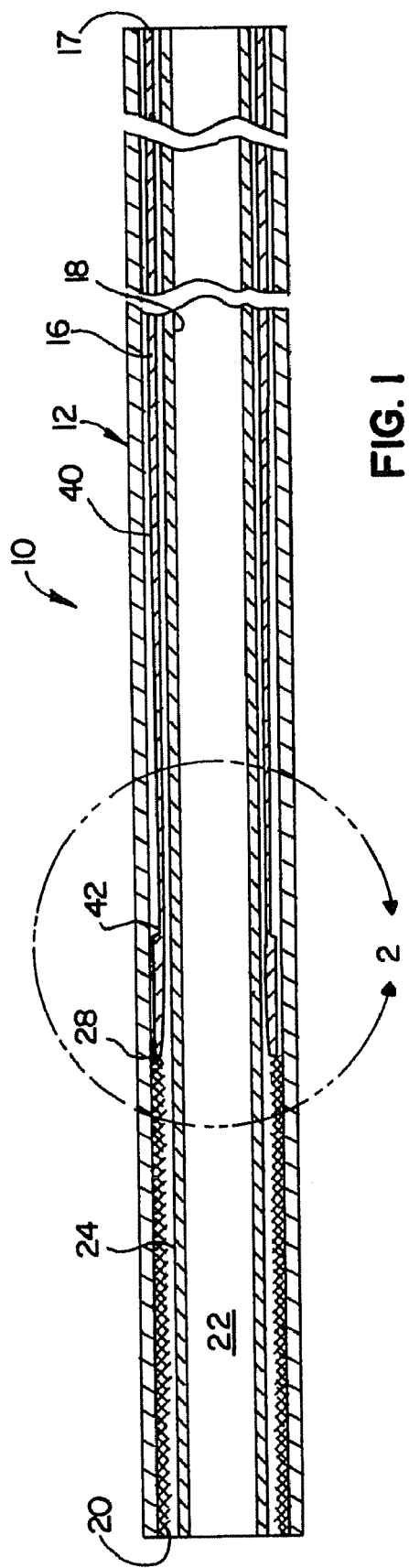
FIG. 1 is a longitudinal sectional view of a delivery system according to one embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the delivery system, as well as the axial ends of various component features. The term "proximal" is used in its conventional sense to refer to the end of the system (or component thereof) that is closest to the operator during use of the system. The term "distal" is used in its conventional sense to refer to the end of the system (or component thereof) that is initially inserted into the patient, or that is closest to the patient during use.

Figure 2:
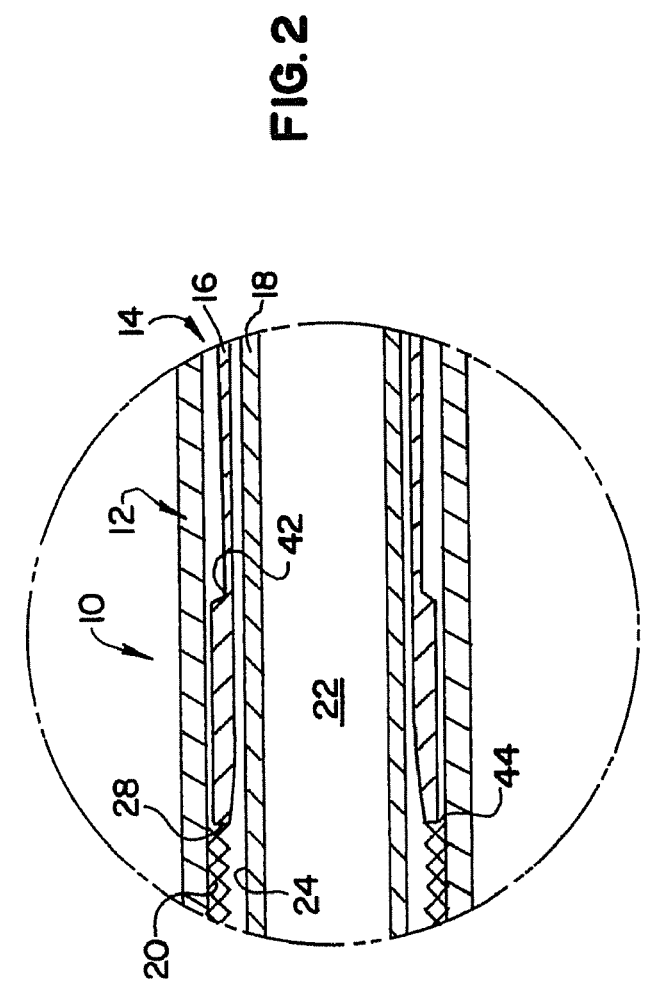
FIG. 2 is an enlarged view of a portion of FIG. 1.

FIG. 1 is a longitudinal sectional view of a delivery system 10 according to one embodiment of the present invention. FIG. 2 is an enlarged view of a portion of the delivery system of FIG. 1. As illustrated, delivery system 10 comprises an introducer sheath 12, and an inner delivery assembly 14. In the embodiment shown, inner delivery assembly 14 comprises coaxial outer 16 and inner 18 tubular members. The figures also illustrate the presence of a medical interventional device, such as stent 20, that is loaded into the delivery system at a distal end of inner delivery assembly 14. A conventional handle (not shown) may be provided at the proximal end of the system.

Introducer sheaths are well known in the medical arts. Optimally, an introducer sheath should be capable of traversing tortuous pathways in the body of the patient without kinking. This generally necessitates that the sheath have sufficient flexibility to negotiate high angle bends, such as the bifurcation into the iliacs. At the same time, the sheath should have sufficient trackability to enable it to enter, and pass into, the target area.

A preferred introducer sheath for use in the inventive system is the FLEXOR® introducer sheath, available from Cook Incorporated, of Bloomington, Ind. The FLEXOR® sheath includes an inner lubricious liner, an outer polymeric jacket, and a coil reinforcement between the inner and outer layers. Typically, the sheath comprises one or more longitudinal segments of decreasing durometer in the distal direction. This sheath provides very favorable flexibility without kinking or compression. One or more radiopaque bands or markers may be incorporated within the sheath material to allow precise location of the sheath's distal tip for positioning accuracy. Those skilled in the art will appreciate that other known introducer sheaths may also be suitable for a particular purpose. The length of the introducer sheath will typically be between about 80 and 150 cm. Preferably, the length of the introducer sheath will be between about 110 and 130 cm, and more preferably, about 125 cm. Those skilled in the art will appreciate, however, that all dimensions provided herein are intended as examples only, and that sheaths and inner delivery assemblies of different dimensions may be substituted for a particular use.

FIG. 3 is a longitudinal sectional view of the inner delivery assembly 14 of delivery system 10. For illustrative purposes, a stent 20 has been loaded onto the distal end of assembly 14. Coaxial outer and inner tubes 16, 18 are preferably immovable relative to each other, or at most, only minimally movable such that the relative positioning of the tubes as shown in the figures is substantially maintained during use of delivery system 10. Outer and inner tubes 16, 18 can be rendered substantially immovable, for example, by utilizing an adhesive or other attachment mechanism that connects the tubes at their respective proximal ends. Alternatively, the adhesive or other attachment mechanism can be applied anywhere along the length of the outer and inner tubes in a manner sufficient for maintaining the respective relative positions substantially as shown in the figure.

Inner tube 18 may have a length the same as, or substantially similar to, the length of the introducer sheath. Inner tube 18 includes a passageway 22 extending therethrough having a diameter sufficient to accommodate a wire guide (not shown). A distal seat portion 24 of inner tube 18 is sized for seating stent 20 on an outer surface thereof. Typically, a soft polymeric tip 19 is positioned at the distal end of inner tube 18 to ease entry into the body.

Outer tube 16 of inner delivery assembly 14 has a length less than the length of inner tube 18. Thus, for example, when a 125 cm introducer sheath is used, the length of inner tube 18 may also be about 125 cm, and the length of outer tube 16 may be about 117 cm. The difference in length between inner tube 18 (125 cm) and outer tube 16 (117 cm) represents the length of seat portion 24 for stent 20. In this case, seat portion 24 and stent 20 each have a length of about 8 cm. The components of delivery system 10 can, of course, be formed to have other lengths so that stents or other medical interventional devices having lengths other than 8 cm can also be delivered via the inventive delivery system 10.

Beginning at proximal end 17 and extending in the distal direction for the major part of its length, outer tube 16 of inner delivery assembly 14 preferably has a generally uniform outer diameter, referred to herein as the "nominal" diameter of tube 16. As described herein, a "major" part of the length of outer tube 16 refers to a length that exceeds one-half of the overall length of outer tube 16. Preferably, the "major" length of outer tube 16 refers to a length of at least about 75% of the length of the tube. The outer profile of a distal portion A (FIG. 3) of outer tube 16 is modified when compared to the nominal diameter of its major length. For the delivery system having the dimensions provided hereinabove, the distal most portion A having the modified profile represents approximately the distal most 16 cm of the outer tube 16. Beginning at the proximal boundary 40 of portion A (which has the nominal outer diameter), and extending in a distal direction therefrom, the outer diameter of outer tube 16 has a gradual inward taper for a distance of between about 10 and 20 cm, preferably about 15 cm, to a minimum diameter point 42. This inwardly tapering portion is designated in FIG. 3 as portion B. There is then a short, or abrupt, outward taper back (over a distance of approximately 0.2 cm) to the nominal diameter. The nominal diameter thereafter extends substantially in the distal direction the remainder (approximately 0.8 cm) of portion C until it terminates in outward flared portion 44. As described herein, a "gradual inward taper" is one that extends from a larger diameter over a relatively large length to a smaller diameter. An "abrupt outward taper" is one that extends from a smaller diameter over a relatively short length, typically not more than about 1 cm, to a larger diameter.

Although it is preferred that outer tube 16 maintains the nominal diameter for the major part of its length prior to the gradual inward taper, this is not necessary in all instances. If desired, a more gradual inward taper of tube 16 that commences from a point proximal to that of boundary 40 up to proximal end 17 may be substituted. Similarly, although it is preferred that the abrupt outward taper occur over a relatively short length (such as 0.2 cm in the example provided), this is not necessary in all instances, and a somewhat less abrupt outward taper may be substituted. Preferably, however, the respective "gradual" and "abrupt" tapers will be in general proportion to those of the inward and outward tapers recited in the example provided.

Outer tube 16 is configured such that it includes a shoulder 28 at its distal end. Preferably, the distal most extension of portion C is also provided with the slight outward flare 44. This is best shown in FIG. 4. As a result, when inner delivery assembly 14 is received in introducer sheath 12 as shown in FIG. 1, the radial extension of flared portion 44 substantially butts against the inner surface of the introducer sheath. In this manner, shoulder 28 and flare 44 act in the nature of a holding, or restraining, band to prevent proximal movement or drifting of stent 20 as introducer sheath 12 is withdrawn in the proximal direction during deployment of the stent.

Typically in a coaxial catheter assembly utilized in a delivery system, a high stress point is created where the inner tube meets the outer tube. This is particularly true in the vicinity of the distal portion of the outer tube. This is due, in part, to the stiffness of the combined tubes being greater than the stiffness of the single inner tube, and, in part, to the stiffness of the medical interventional device, such as stent 20, seated on the inner tube. As stated, when the catheter assembly is required to go around a high angle bend, such as the aforementioned bifurcation into the iliacs, kinking and decreased trackability are prone to occur due to the high stress point described above, as well as any other stress risers that may form or otherwise be present. In the embodiment of the inventive arrangement described, the stress at the high stress point is reduced by providing the gradual inward taper of the outer tube diameter to the smaller diameter in the vicinity of the distal end of the inner delivery assembly, and then providing the abrupt outward taper in the inverse direction. This arrangement will distribute the stress more evenly, and improve trackability.

Tapered portion B may be formed in outer tube 16 by any conventional means. Preferably, tube 16 is ground to the desired tapered configuration, such as with use of a conventional grinder that can be programmed to grind different profiles, a process often referred to as centerless grinding. Alternatively, other known means for forming a tapered catheter, such as extrusion, may be employed. The distal flare 44 of tube 16 may be formed by conventional means, such as by heating the portion to be flared (e.g., via a conventional flare gun) and forming the desired flare on the heated portion. The flare need not have any specific configuration, as long as the configuration is suitable for acting as a pusher or holder against the stent, such that proximal drift of the stent is inhibited upon withdrawal of the introducer sheath. In general, it is preferred to shield as much of the proximal end of the stent area as possible with the flare.

The dimensions of the introducer sheath 12 and the outer and inner tubes 16, 18 will, of course, depend upon the intended use of the delivery system 10. The following non-limiting example is provided to illustrate the relative dimensions of the various component features for a representative use. In this example, the length of the introducer sheath is 125 cm. The outer diameter (OD) of the sheath will, of course, be dependent upon the vessel to be traversed. In most cases the OD of the introducer sheath will be between about 0.069 and 0.10 inch (1.75 and 2.54 mm), and in the example provided herein, about 0.092 inch (2.34 mm). The inner diameter (ID) of the sheath will, in most cases, be between about 0.0535 and 0.090 inch (1.36 and 2.29 mm), and in the example described herein, about 0.076 inch (1.93 mm). As stated, these dimensions are merely exemplary of possible dimensions for a particular use. Those skilled in the art can readily select appropriate dimensions for a specific use.

With reference to the components of the inner delivery system 14, the ID of the inner tube 18 may be about 0.040 inch (1.02 mm), or large enough such that a wire guide can be accommodated therethrough. The 0.040 inch ID is large enough to accommodate a standard wire guide of about 0.035 inch (0.89 mm) diameter. The OD of the inner tube may be about 0.051 inch (1.30 mm). The nominal OD of outer tube 16 may be about 0.071 inch (1.80 mm), and the ID of the tube may be about 0.058 inch (1.47 mm). The minimum OD of the outer tube at point 42 of maximum taper may be about 0.064 inch (1.63 mm). The maximum OD at flared portion 44 may be about 0.075 inch (1.91 mm), or in other words, only slightly less than the 0.076 inch (1.93 mm) ID of the introducer sheath. Once again, those skilled in the art will appreciate that these dimensions are merely exemplary of possible dimensions for a particular use, and that appropriate dimensions can be readily selected for a specific intended use.

One specific example of a taper of outer tube 16 has been provided above. In that non-limiting example, the outer diameter of outer tube 16 has a gradual inward taper (portion "B") for a distance of about 15 cm, to a minimum diameter point 42. There is then a short outward taper of approximately 0.2 cm to the nominal diameter, which thereafter extends substantially in the distal direction the remainder (approximately 0.8 cm) of portion C. Those skilled in the art will appreciate that these dimensions are also merely exemplary of possible dimensions for a particular use, and that appropriate dimensions can be readily selected for a specific intended use. Typically, virtually any taper into the nominal diameter of the outer tube will provide at least some enhanced flexibility to the tube, and serve to distribute the stress more evenly than before. A skilled artisan may utilize routine experimentation to determine an optimal taper for a particular use, which taper may include a more, or less, gradual inward taper than described in the example above, and a more, or less, gradual outward taper. Such a taper will, in many instances, be dependent upon the respective compositions of the sheath and inner delivery assembly, as well as the anticipated degree of bend of the sheath and assembly as they pass through one or more bends in a tortuous body passageway.

Outer and inner tubes 16, 18 of inner delivery assembly 14 are preferably formed of a composition having sufficient strength, flexibility, and resistance to compression to traverse tortuous areas of the anatomy. One particularly preferred composition is PEEK (polyetheretherketone). PEEK is a particularly favored composition for medical use based upon the properties recited above, as well as its biocompatibility and resistance to degradation under extreme conditions. Those skilled in the art will appreciate, however, that other compositions may also be suitable for a particular application. Non-limiting examples of other suitable catheter compositions include nylon (polyamide), polyether block amides, and PET (polyethylene terephthalate).

FIGS. 5 and 6 illustrate an alternative inner delivery assembly 114 for use in the inventive delivery catheter 10. Introducer sheath 12 has been omitted from these figures to better illustrate the features of the inner delivery assembly. FIG. 5 is a longitudinal sectional view of the inner delivery assembly 114. FIG. 6 is an enlarged view of a portion of FIG. 5. In this embodiment, inner delivery assembly 114 comprises coaxial outer 116 and inner 118 tubes. The figures also illustrate the presence of a stent 20 that is loaded into the delivery system at a distal end of inner delivery assembly 114.

Inner tube 118 includes a passageway 122 extending therethrough having a diameter sufficient to accommodate a wire guide (not shown). A distal portion 124 of inner tube 118 is sized for seating stent 20 on an outer surface thereof. Outer tube 116 of inner delivery assembly 114 has a length less than the length of inner tube 118, which difference in length represents the length of distal seat portion 124 for stent 20. The components of inner delivery assembly 114 not specifically described are generally the same as or similar to corresponding components in the previously-described inner delivery assembly 14.

In the preferred embodiment shown, outer tube 116 extends in the distal direction from proximal end 117 at a generally uniform "nominal" diameter for the major part of its length. The outer profile of a distal portion X of outer tube 116 (FIG. 5) is modified when compared to the nominal diameter of its major length. In this embodiment, the distal most portion X begins at point 140, and exhibits a gradual inward taper to a minimum diameter at the distal end 142 of outer tube 116. Alternatively, the taper may commence at a point proximal to point 140 if an even more gradual taper is desired.

A holder band 150 for the medical device, such as stent 20, is fitted over the distal portion of outer tube 116. In the preferred embodiment shown in FIG. 6, holder band 150 has an inner diameter that increases from a smaller ID at the distal end 152 to a larger ID at proximal end 154. Preferably, at least a portion of the distal length of holder band 150 extends distal of outer tube distal end 142. In a preferred embodiment, at least a portion of the interior surface of holder band 150 has an outward taper that substantially corresponds to the inward taper of outer tube 116. When fitted onto inner delivery assembly 114 as shown, the outer diameter of holder band 150 will preferably be substantially the same as the nominal outer diameter of outer tube 116. The respective outer diameters of the outer tube and the holder band will preferably be similar to, but slightly smaller than, the inner diameter of the introducer sheath (not shown). As a result, the outer diameter of the holder band will be as close to the inner diameter of the introducer sheath as possible, without causing interference or friction upon relative movement with the introducer sheath.

Holder band 150 terminates in the distal direction in a shoulder 156. Shoulder 156 is preferably sized and configured to inhibit stent 20 from protruding or otherwise drifting in the proximal direction beyond shoulder 156 upon withdrawal of the introducer sheath during deployment of the stent, in the same manner as shoulder 28 in the previous embodiment. The holder band need not be formed to have the identical configuration described herein, as long as the selected configuration provides enhanced flexibility to the overall assembly, and will suffice to maintain, or hold, the position of the stent as described. Use of a separate element, such as the holder band, may provide enhanced flexibility in a particular case when compared to the use of an integral tube as described in the previous embodiments. Utilizing a separate element also provides the ability to use different materials for this portion of the assembly, such as a more flexible composition, if desired.

Holder band 150 is preferably formed of a flexible polymeric material such as nylon. Other known materials, such as polymers and non-ferrous metals, having favorable compression strength and flexibility may be substituted. The tapered portion may be formed in outer tube 116 in the same manner in which the taper is formed in outer tube 16. A flare may be formed at the distal end of the holding band in the same manner as the flare in outer tube 16.

While these features have been disclosed in connection with the illustrated preferred embodiments, other embodiments of the invention will be apparent to those skilled in the art that come within the spirit of the invention as defined in the following claims.

The invention claimed is:

1. A delivery assembly for use in the delivery of a medical device to a target site within the body of a patient, comprising:
an inner tubular member having a proximal end and a distal end, at least a distal portion of said inner tubular member having a diameter such that said medical device is receivable thereover, and an outer tubular member having a proximal end and a distal end, said outer tubular member generally coaxial with the inner tubular member and having a length such that said outer tubular member distal end terminates proximal to said inner tubular member distal portion, said outer tubular member having a first outer diameter at said proximal end and having a gradual inwardly tapered portion in a distal direction to a second outer diameter, and having an abrupt outward taper in the distal direction from said second diameter.

2. The delivery assembly of claim 1, wherein said first outer diameter extends for a major length of said outer tubular member to a first diameter boundary point, said outer tubular member having said gradual inward taper in the distal direction from said boundary point to said second outer diameter.

3. The delivery assembly of claim 2, wherein said first outer diameter extends in the distal direction at least 75% of the length of the outer tubular member.

4. The delivery assembly of claim 1, wherein said abrupt outward taper terminates when said outer tubular member returns substantially to said first outer diameter.

5. The delivery assembly of claim 1, wherein said distal end of said outer tubular member comprises a shoulder.

6. The delivery assembly of claim 1, wherein said distal end of said outer tubular member comprises an outwardly directed flare.

7. The delivery assembly of claim 1, wherein said distal end of said outer tubular member comprises a shoulder and an outwardly directed flare.

8. The delivery assembly of claim 1, wherein at least one of said inner and outer tubular members is formed from PEEK.

9. A system for delivery of a medical device to a target site within the body of a patient, comprising:

an introducer sheath having a proximal end, a distal end, and a passageway extending therebetween, said introducer sheath having a length sufficient for insertion through a pathway in the body of the patient from an entry site to the target site; and a delivery assembly receivable within said sheath passageway for carrying said medical device, said delivery assembly comprising an inner tubular member having a proximal end and a distal end, at least a distal portion of said inner tubular member having a diameter such that said medical device is receivable thereover, and an outer tubular member having a proximal end and a distal end, said outer tubular member generally coaxial with the inner tubular member and having a length such that said outer tubular member distal end terminates proximal to said inner tubular member distal portion, said outer tubular member having a first outer diameter at said proximal end and extending for a length of said outer tubular member to a first diameter boundary point, said outer tubular member having a gradual inward taper in the distal direction from said boundary point to a second outer diameter, and having an abrupt outward taper in the distal direction from said second diameter.

10. The delivery system of claim 9, wherein said abrupt outward taper terminates when said outer tubular member returns substantially to said first outer diameter.

11. The delivery system of claim 9, wherein said distal end of said outer tubular member comprises a shoulder.

12. The delivery system of claim 9, wherein said distal end of said outer tubular member comprises an outwardly directed flare.

13. The delivery system of claim 12, wherein a radial outward extension of said flare substantially abuts against a surface of said introducer sheath passageway.

14. The delivery system of claim 9, wherein said first outer diameter extends in the distal direction at least 75% of the length of the outer tubular member.

15. The delivery system of claim 14, wherein said introducer sheath and said inner tubular member each have a length between about 110 and 130 cm, and said gradual inward taper of said outer tubular member extends in said distal direction for a length between about 10 and 20 cm.

* * * * *

UNITED STATES PATENT AND TRADEMARK OFFICE
CERTIFICATE OF CORRECTION

PATENT NO. : 7,566,342 B2  
APPLICATION NO. : 11/965210  
DATED : July 28, 2009  
INVENTOR(S) : Fred T. Parker et al.

It is certified that error appears in the above-identified patent and that said Letters Patent is hereby corrected as shown below:

On the Title Page:

(73) Assignee, please add the following additional named Assignee: -- William Cook Europe ApS, Bjaeverskov (DK) --

Signed and Sealed this

Twenty-seventh Day of October, 2009

David J. Kappos  
*Director of the United States Patent and Trademark Office*